United States Patent
Wood et al.

(10) Patent No.: US 10,575,732 B2
(45) Date of Patent: Mar. 3, 2020

(54) BODY-WORN THERMOMETRY SOLUTIONS

(71) Applicant: Welch Allyn, Inc., Skaneateles Falls, NY (US)

(72) Inventors: Robert J. Wood, Syracuse, NY (US); Raymond A. Lia, Auburn, NY (US); Jon R. Salvati, Auburn, NY (US); Steven D. Baker, Beaverton, OR (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 323 days.

(21) Appl. No.: 15/395,486

(22) Filed: Dec. 30, 2016

(65) Prior Publication Data

US 2018/0184903 A1 Jul. 5, 2018

(51) Int. Cl.
*A61B 5/00* (2006.01)
*A61B 5/0408* (2006.01)

(52) U.S. Cl.
CPC .......... *A61B 5/0008* (2013.01); *A61B 5/0022* (2013.01); *A61B 5/0024* (2013.01); *A61B 5/04087* (2013.01)

(58) Field of Classification Search
CPC ... A61B 5/0008; A61B 5/0022; A61B 5/0024; A61B 5/04087; G01K 1/165; G01K 7/427
See application file for complete search history.

(56) References Cited

U.S. PATENT DOCUMENTS

| 9,101,271 | B2 | 8/2015 | Sattler | |
|---|---|---|---|---|
| 2008/0018467 | A1* | 1/2008 | Estevez | G06K 19/0707 340/572.1 |
| 2012/0024833 | A1* | 2/2012 | Klewer | A61B 5/0008 219/211 |
| 2012/0143079 | A1* | 6/2012 | Lia | A61B 5/01 600/549 |

* cited by examiner

*Primary Examiner* — Patrick Fernandes
(74) *Attorney, Agent, or Firm* — Lee & Hayes, P.C.

(57) ABSTRACT

An example system includes a patch defining a first surface and a second surface opposite the first surface. The first surface is removably attachable to skin of a subject. The patch includes a conductor associated with the first surface, a first sensor configured to determine a temperature of the conductor, and a second sensor configured to determine an additional temperature. The first sensor is separated from the second sensor by material having a known thermal resistance. The patch also includes a transmitter operably connected to the first and second sensors.

19 Claims, 6 Drawing Sheets

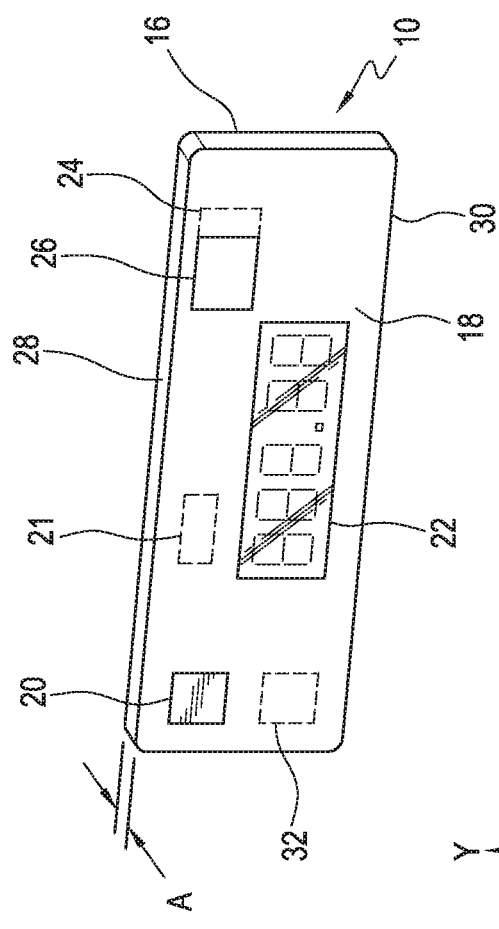
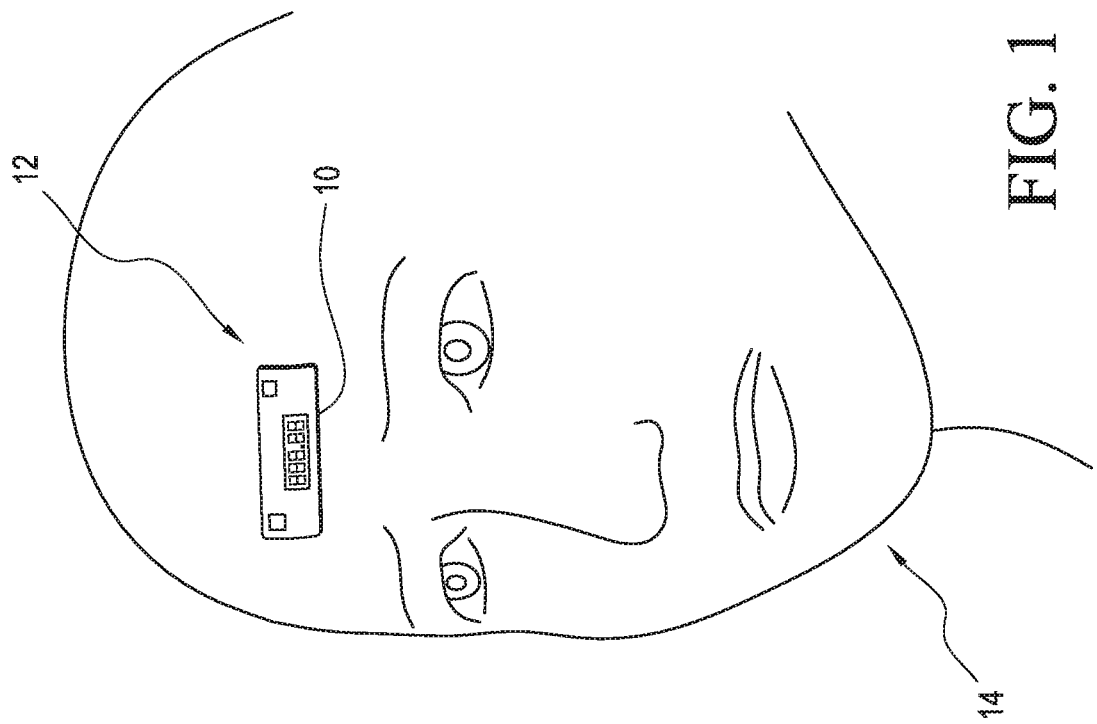
FIG. 2
FIG. 1

BODY-WORN THERMOMETRY SOLUTIONS

STATEMENT REGARDING FEDERALLY SPONSORED RESEARCH OR DEVELOPMENT

None

REFERENCE TO A "SEQUENCE LISTING"

Not applicable

BACKGROUND OF THE INVENTION

Field of the Invention

The present disclosure generally relates to devices and methods for temperature determination and, in particular, to devices and methods for determining a core temperature, such as a sub-skull temperature, of a subject.

Description of Related Art

Internal body temperature is widely used by physicians and other healthcare professionals as an indicator of a person's health. In most healthcare facilities, various non-invasive techniques may be utilized to measure internal temperature before, during, and/or after treatment. Such techniques typically include the use of oral, rectal, tympanic, or axial thermometers. These instruments are useful in providing a substantially instantaneous temperature reading, but are not generally used to provide relatively long-term monitoring of a patient's temperature. However, such long-term temperature monitoring can be useful to healthcare professionals when providing treatment. Such devices are not well-suited for these types of temperature measurements since, for example, disposing a thermometer in the mouth of a patient for long periods of time can cause discomfort and can be otherwise cumbersome. Moreover, often the condition of the patient may make it difficult or impossible to access, for example, the mouth, rectum, and/or other areas of the body where temperature is typically measured with such devices.

To overcome some of these problems, devices have been developed enabling continuous monitoring of patient temperature. Such devices are typically in the form of an adhesive patch or bandage-like structure having one or more temperature sensors. Such devices are typically adhered to the patient's skin overlaying a portion of the temporal artery. These devices, however, are characterized by deficiencies making them undesirable for use in many patient treatment settings. For example, such devices must be placed in close proximity to the temporal artery in order to obtain an accurate temperature measurement. However, since the temporal artery is beneath the skin, and is not easily visible, such devices are often mispositioned on the patient. Such mispositioning can have adverse affects on the accuracy of the temperature measurement obtained using such devices. In addition, the temperature at the skin surface can be significantly influenced by the ambient temperature and often does not correlate well with core body temperature. Moreover, ambient conditions can often degrade the accuracy of temperature measurements made by such devices.

The example embodiments of the present disclosure overcome one or more of the deficiencies described above.

BRIEF SUMMARY OF THE INVENTION

In an example embodiment of the present disclosure, a system includes a patch defining a first surface and a second surface opposite the first surface, wherein the first surface is removably attachable to skin of a subject. In such a system, the patch includes a conductor associated with the first surface, a first sensor configured to determine a temperature of the conductor, and a second sensor configured to determine an additional temperature, wherein the first sensor is separated from the second sensor by material having a known thermal resistance. The patch also includes a radio-frequency identification "RFID") antenna operably connected to the first and second sensors. The RFID antenna may be configured to provide power to the first and second sensors, and to provide at least one of the first temperature, the additional temperature, or a core temperature of the subject to an RFID reader. As used in this specification, RFID refers to any system whereby energy from a remote device is used in whole, or in part to power the temperature circuit and/or to create a data transmission. Data transmission may be through an active radio frequency ("RE") transmitter or through modulation of the load on the received, powering signal, or any other method of modulating a signal onto a carrier. Standards such as near-field communication ("NEC") are included within this definition as would be a Bluetooth beacon that is powered in whole or in part by the remote device. The RFID antenna may have various forms including, but not limited to electric antennas, magnetic antennas, dipoles, coils, loops, monopoles, microstrips, printed circuit board antennas, and the like.

In another example embodiment of the present disclosure, a system includes a patch defining a first surface and a second surface opposite the first surface, wherein the first surface is removably attachable to skin of a subject. In such a system, the patch includes a conductor associated with the first surface, a first thermistor configured to determine a temperature of the conductor, and a second thermistor configured to determine an additional temperature, wherein the first thermistor is separated from the second thermistor by a portion of the patch having a known thermal resistance. Such a patch also includes a wireless transmitter operably connected to the first and second thermistors, wherein the transmitter is configured to wirelessly provide at least one of the first temperature, the additional temperature, or a core temperature of the subject to a device separate from the patch. Alternately, the system might transmit the directly measured parameter or parameters of the temperature sensor, for example the resistance of a thermistor, the resistance of a thermocouple, or the forward voltage of a diode. Transmitting the directly measured parameter or parameters of the temperature sensor is considered the same as transmitting the temperature since there is a 1:1 relationship between the directly measured parameter and the temperature. For example, if using a thermistor, the direct measure is the resistance and the Steinhart-Hart equation may be used to calculate the temperature, and this calculation may be done by the patch 10 or the receiver, or some computing component upstream from the server. In this specification, the term transmitting a temperature includes transmitting the directly measured parameter or transmitting the specific temperature calculated from the directly measured parameter. Alternately, a neural network or other machine learning algorithm may be used to determine the temperature. For example, and assuming thermistors are used to detect the temperature, by placing the patch on a patient, recording the resistances of the various thermistors and the core temperature (measured for example using a Foley catheter), a neural network may be trained to determine the core temperature using methods familiar to those well versed in the art.

In still another example embodiment of the present disclosure, a method of manufacturing a system includes providing a patch defining a first surface and a second surface opposite the first surface, wherein the first surface is removably attachable to skin of a subject. The method also includes connecting a conductor to the patch at a location spaced from the second surface, and operably connecting a first sensor to the patch, the first sensor being configured to determine a temperature of the conductor. The method further includes operably connecting a second sensor to the patch, the second sensor being spaced from the first sensor by a portion of the patch having a known thermal resistance, the second sensor being configured to determine an additional temperature. The method also includes connecting a wireless transmitter to the patch, the wireless transmitter being operably connected to the first and second sensors, and being configured to wirelessly provide at least one of the first temperature, the additional temperature, or a core temperature of the subject to a device separate from the patch.

BRIEF DESCRIPTION OF THE SEVERAL VIEWS OF THE DRAWING(S)

FIG. 1 illustrates a patch positioned on a forehead of a subject according to an example embodiment of the present disclosure.

FIG. 2 illustrates a patch according to an example embodiment of the present disclosure.

Figure 3:
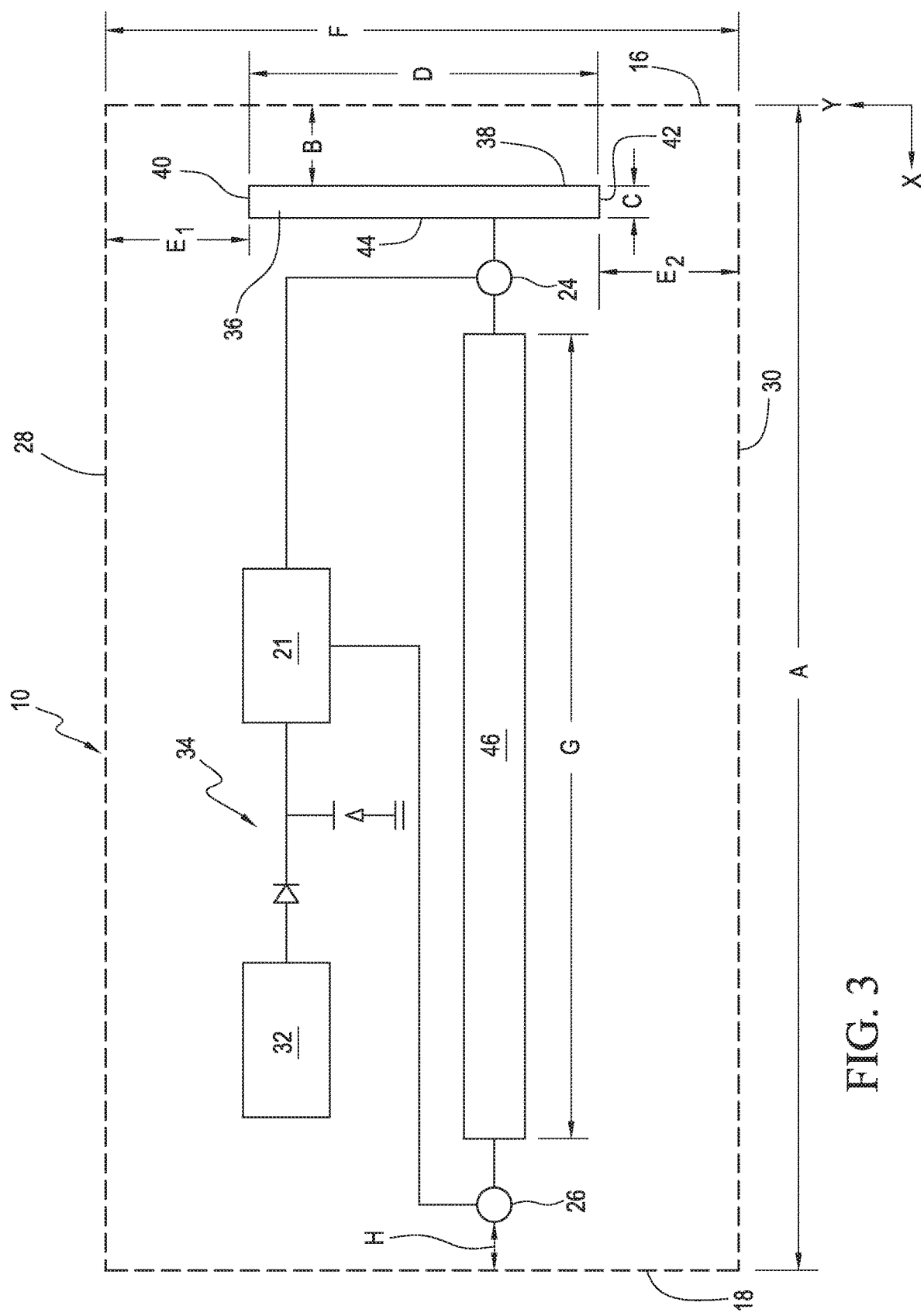

FIG. 3 provides a schematic illustration of a patch, according to an example embodiment of the present disclosure.

Figure 4:
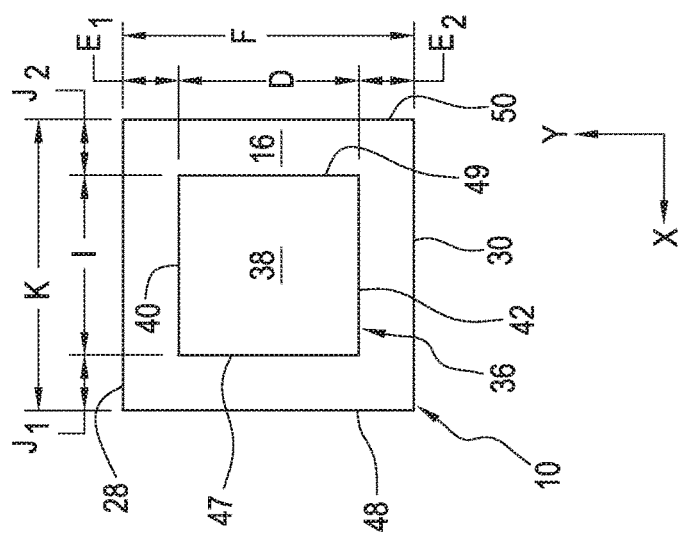

FIG. 4 illustrates a first surface of a patch according to an example embodiment of the present disclosure.

Figure 5:
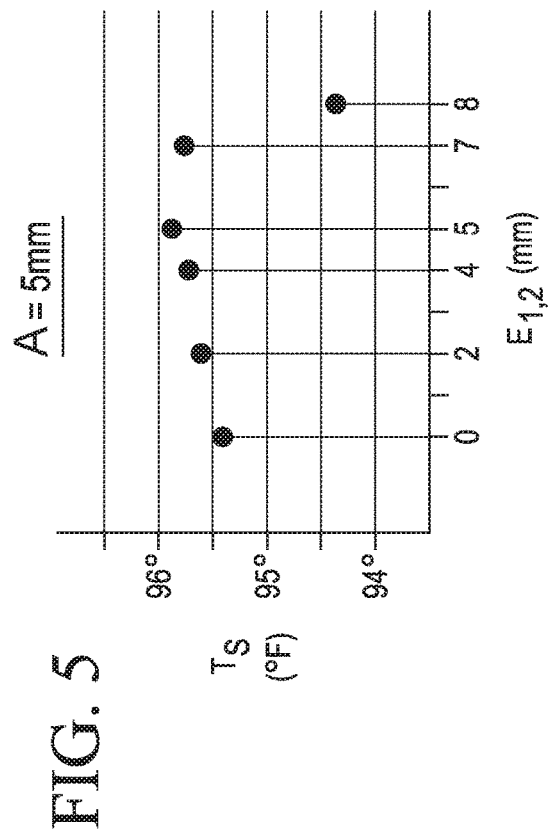

FIG. 5 illustrates a temperature plot according to an example embodiment of the present disclosure.

Figure 6:
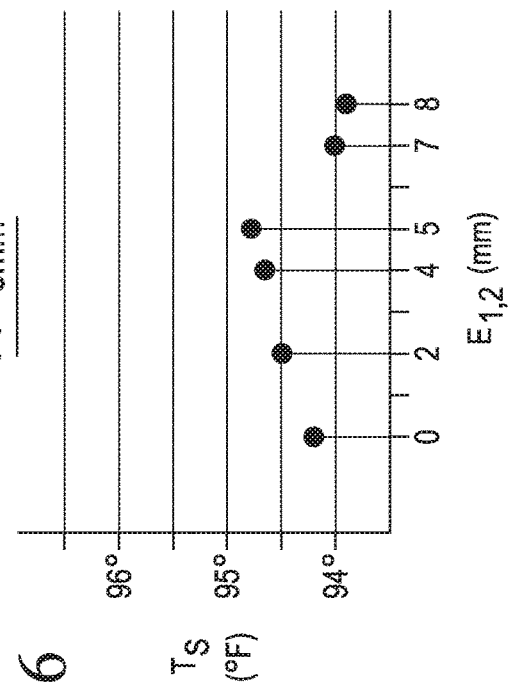

FIG. 6 illustrates a temperature plot according to another example embodiment of the present disclosure.

Figure 7:
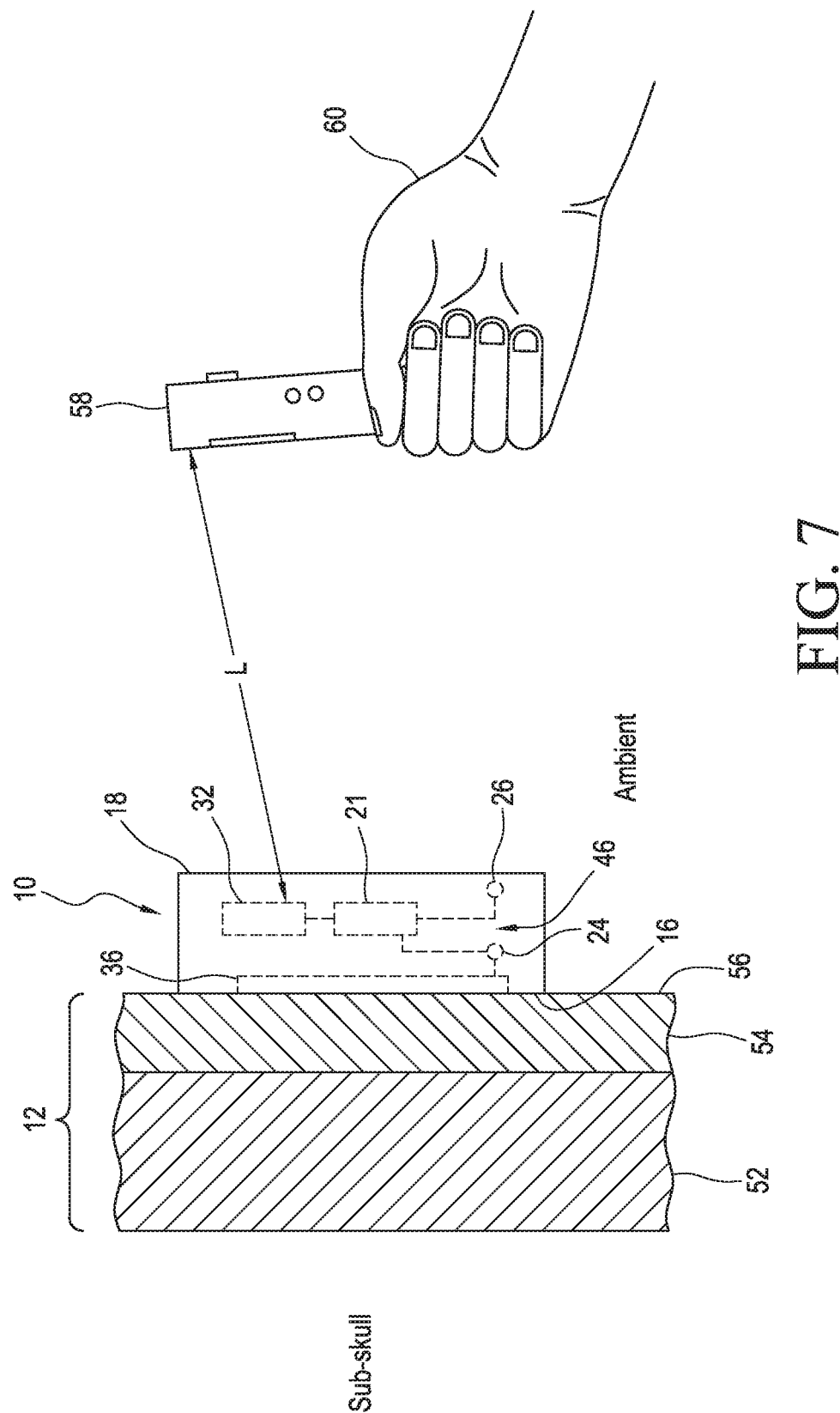

FIG. 7 illustrates a partial cross-section of a forehead of a subject with a patch connected thereto, according to another example embodiment of the present disclosure.

Figure 8:
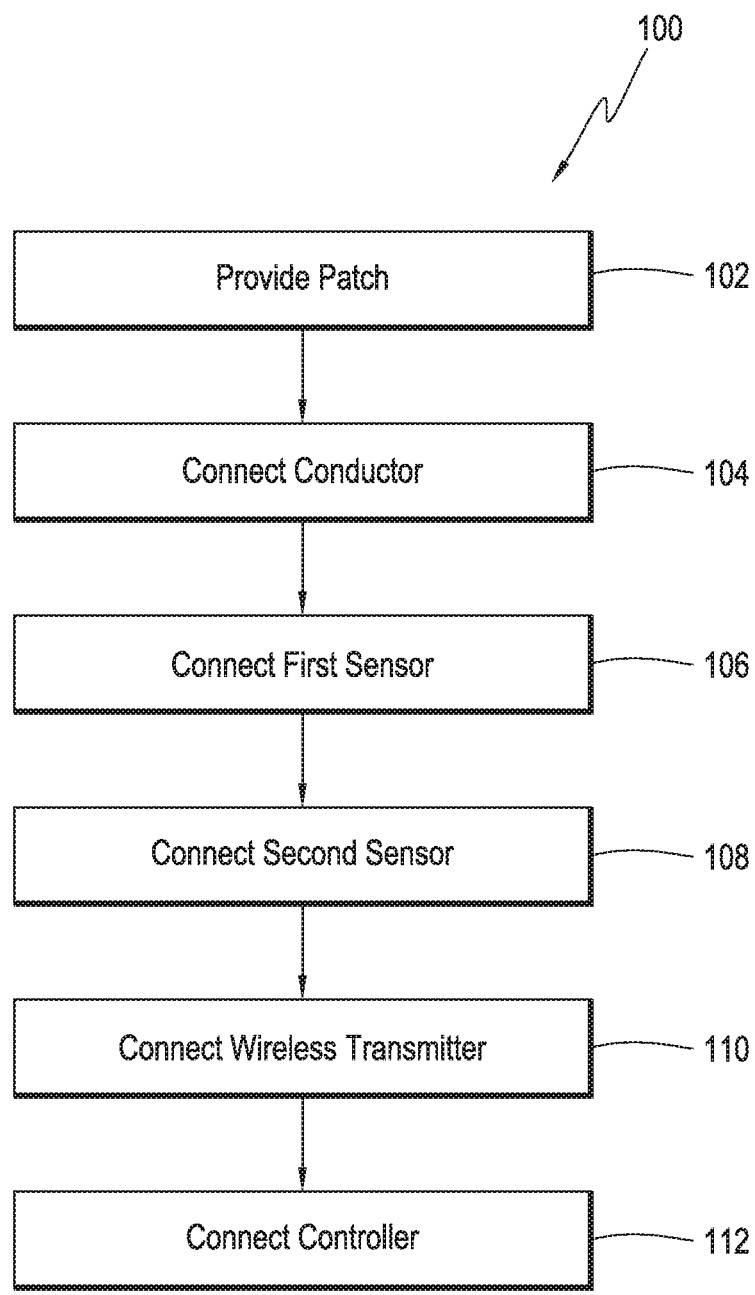

FIG. 8 provides a flowchart illustrating an example method of the present disclosure.

Figure 9:
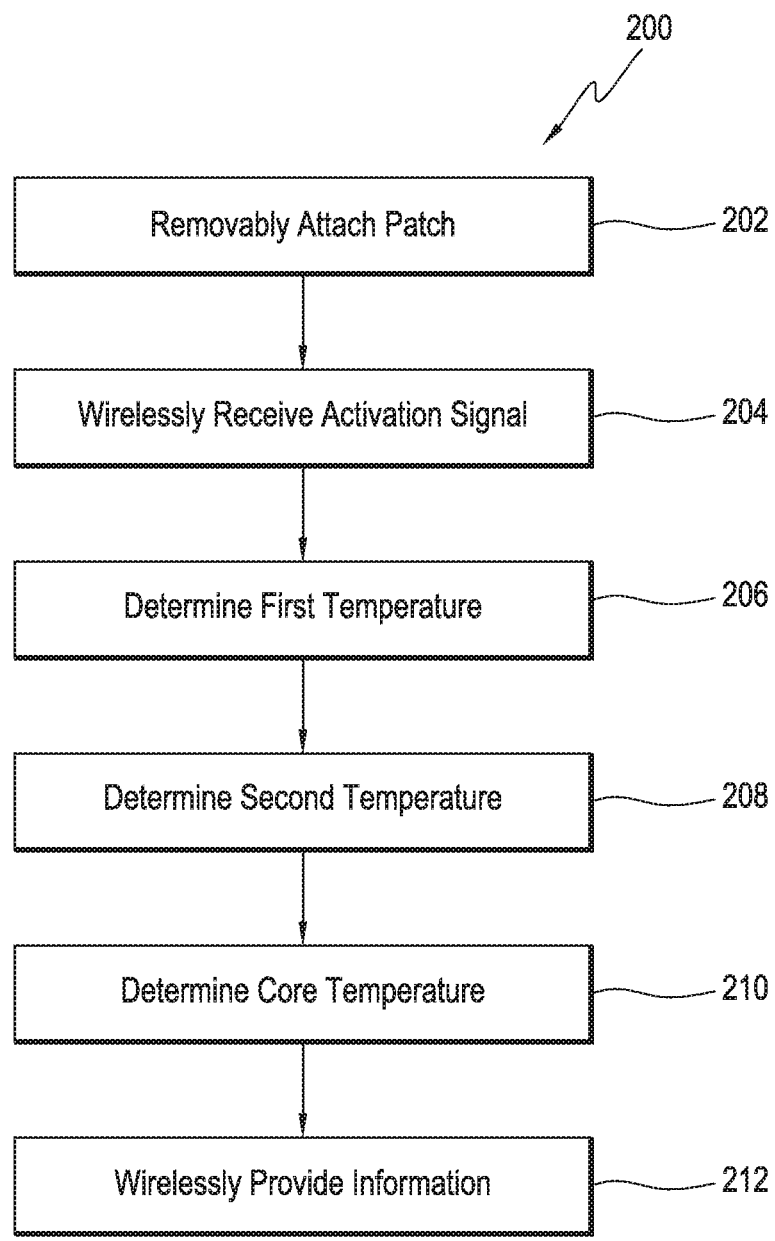

FIG. 9 provides a flowchart illustrating another example method of the present disclosure.

DETAILED DESCRIPTION OF THE INVENTION

The various figures described herein illustrate example temperature measurement systems, devices, and/or patches 10 useful in determining the temperature of a subject 14. These figures also illustrate temperature plots and methods associated with such systems. As described herein, and as shown in FIG. 1, a "subject" 14 may be, for example, a human being in need of medical treatment or diagnosis. In such embodiments, a patch 10 of the present disclosure may be connected, affixed, disposed, adhered, and/or otherwise connected to a forehead 12 of the subject 14. For example, the patch 10 may be temporarily and/or removably connected to and/or may temporarily contact at least a portion of the forehead 12 during use. Positioning the patch 10 on the forehead 12 of the subject 14 may be advantageous when determining a temperature of the subject 14 since the forehead 12 is relatively isolated from veins, arteries, and/or other blood flow passages. The flow of blood through such anatomical structures may cause error in temperature measurements that are taken using the patch 10 or other nonintrusive devices. Such errors may, in turn, affect the accuracy of a core temperature of the subject 14 that is calculated and/or otherwise determined based at least partly on such temperature measurements.

The core temperatures of the subject 14 described herein may be, for example, a sub-skull temperature and/or any other like internal body temperature of the subject 14. For example, the core temperature may comprise the internal temperature of the subject 14 distal to the frontal portion of the skull. As referred to herein, the forehead 12 may comprise the frontal skull bone 52 and the layer of skin 54 positioned proximal and/or overlaying the skull bone 52 (FIG. 7). In further examples, other body positions and/or measurement sites may be used, such as above the sternum, or directly above an artery.

As shown in at least FIG. 2, the patch 10 may define at least two surfaces and, in an example embodiment, the patch 10 may define a first surface 16 configured to at least temporarily contact and/or be removably attached to the forehead 12 of the subject 14. The patch 10 may also include a second surface 18 disposed opposite the first surface 16 and configured to be exposed to ambient conditions such as, for example, to ambient air or other like environments in a hospital and/or other healthcare facility.

As shown in FIGS. 2 and 3, the patch 10 may include one or more components configured to assist in calculating a sub-skull temperature and/or other core temperature based on a measurement of heat flow. For example, the patch 10 may include one or more operator interfaces 20. Such operator interfaces 20 may include one or more buttons, switches, keypads, dials, knobs, and/or other like devices configured to assist in controlling one or more functions of the patch 10. Such operator interfaces 20 may be useful in, for example, energizing and/or deenergizing one or more components of the patch 10, toggling through and/or selecting one or more modes of operation or display, enabling and/or disabling one or more alarms or signals associated with patch operation, initiating a single instantaneous sub-skull temperature calculation, initiating a substantially continuous and/or repeating sub-skull temperature calculation, and/or other like modes, functions, or operations.

In an example embodiment, the patch 10 may include one or more controllers 21, and each of the operator interfaces 20 may be functionally, operably, electrically, and/or otherwise connected to the controller 21. At least one of the additional components of the patch 10 may also be similarly connected to the controller 21, and the controller 21 may be configured to control the operation of each such component. In an example embodiment, the controller 21 may be configured to receive signals, information, measurements, and/or other data from one or more sensors of the patch 10, and to calculate a sub-skull temperature and/or other core temperature of the subject 14 based on the information received. The controller 21 may also be configured to execute one or more commands and/or control programs. For example, the controller 21 may be programmed to initiate one or more alarms in response to calculating a sub-skull temperature and/or other core temperature that is greater than or equal to a predetermined threshold temperature. In addition, the controller 21 may be configured to initiate such an alarm during a substantially continuous sub-skull temperature and/or other core temperature calculation operation if the calculated temperature increases and/or decreases at a rate that is greater than or equal to a predetermined threshold temperature change rate. The controller 21 may also initiate such an alarm to indicate that a location of the patch 10 should be changed, and such a location change alarm may be initiated in response to one or more sensed metrics indicative of blood flow at the forehead skin 54.

In an example embodiment, the patch 10 may also include one or more displays 22. The display 22 may be, for example, a liquid crystal diode (LCD) screen, a light emitting diode (LED) display, a digital read-out, a touchscreen, and/or any other like display device. The display 22 may be configured to, for example, indicate the calculated sub-skull temperature of the subject 14 during operation of the patch 10. The display 22 may be configured to display the calculated sub-skull temperature and/or other core temperature substantially instantaneously and/or substantially continuously depending on the mode of operation of the patch 10. The display 22 may also be configured to indicate the mode of operation of the patch 10 (for example, continuous or instantaneous modes of temperature calculation), as well as whether one or more threshold temperatures, threshold temperature change rates, and/or sensed blood flow metric thresholds have been met or exceeded. As shown in FIGS. 1 and 2, the display 22 may be, for example, a substantially numerical digital display, and may also be configured to display any other typical operating information such as, for example, text, a temperature vs. time graph, or other information. In some embodiments, one or more components of the patch 10 described herein, such as the display 22 or the operator interfaces 20 may be omitted.

The patch 10 may also include at least one sensor. For example, the patch 10 may include a first sensor 24 disposed at or proximate the first surface 16. In an example embodiment, the sensor 24 may be embedded within the patch 10 so as to be integral with the patch 10. Alternatively, the sensor 24 may be substantially internal to the patch 10 such that the sensor 24 may be positioned and/or otherwise configured to sense a characteristic of the first surface 16 and/or a characteristic of a portion or component of the patch 10 associated with the first surface 16. For example, the sensor 24 may be positioned and/or otherwise configured to sense a temperature of the first surface 16 of the patch 10 while the first surface 16 is in contact with and/or attached to the forehead 12. Such a sensor 24 may comprise, for example, a thermocouple, a thermistor, a thermometer, a resistance temperature detector (RTD), diode, and/or any other like device useful in measuring temperature. In additional example embodiments, such a sensor 24 may comprise any temperature-sensitive material or coating known in the art.

In an example embodiment, the sensor 24 may be substantially exposed to and/or disposed in contact with the skin 54 of the forehead 12 while the first surface 16 of the patch 10 is in contact with the forehead 12. Alternatively, the first surface 16 may include a relatively thin layer, wall, film, and/or other like barrier extending between the skin 54 and the sensor 24 while the first surface 16 is in contact with the forehead 12. Such a barrier may form at least a portion of the first surface 16. In such an example embodiment, the thermal resistance of such a barrier may be substantially negligible so as to maximize the accuracy of the one or more measurements made by the sensor 24. Alternatively, the thermal resistance of the barrier may be known or empirically determined, and this thermal resistance may be taken into account when calculating the sub-skull temperature and/or other core temperature of the subject 14.

In example embodiments in which the patch 10 includes such a barrier, the sensor 24 may be configured to sense, measure, and/or otherwise detect one or more properties, conditions, and/or characteristics of the barrier. As will be described in greater detail below, in some embodiments the patch 10 may also include a conductor associated with the first surface 16. In such embodiments, the first sensor 24 may be configured to determine a temperature and/or other characteristics of the conductor. Additionally, in some embodiments in which the patch 10 includes a conductor, the barrier described above may at least partially overlay the conductor, or the barrier may be omitted.

The patch 10 may also include at least one additional sensor, such as a second sensor 26. In some example embodiments, the second sensor 26 may be substantially identical to the first sensor 24. As shown in, for example, FIGS. 2 and 3, the sensor 26 may be disposed at and/or proximate to the second surface 18. In an example embodiment, the sensor 26 may be exposed to ambient conditions, while in additional example embodiments, the second surface 18 may include a layer, wall, film, and/or barrier (not shown) similar to that described above with regard to the first surface 16. In such an example embodiment, the barrier may extend between the sensor 26 and the ambient environment to protect the sensor 26 from contaminants, wet conditions, and/or other potentially damaging or harmful environmental elements. Similar to the barrier discussed above with regard to the first surface 16, a like barrier may form at least a portion of the second surface 18 and may have a substantially negligible thermal resistance so as not to hinder the accuracy of measurements obtained by the sensor 26. Alternatively, the thermal resistance of such a barrier may be taken into account when calculating the sub-skull temperature.

Although shown in FIGS. 2 and 3 as including two sensors 24, 26, in additional example embodiments, the patch 10 may include any number of additional sensors (not shown) configured to assist in sensing conditions of the subject 14 and/or the patch 10 such as temperature, blood pressure, pulse oximetry, heart rate, and/or other like metrics. Such additional sensors may be disposed at or along any of the surfaces 16, 18 of the patch 10 and/or at any other useful position along and/or within the patch 10. For example, the patch 10 may also include a third surface 28 that extends substantially perpendicular to the first surface 16. The patch 10 may also include a fourth surface 30 opposite the third surface 28. In such embodiments, the patch 10 may have a thickness A extending from the first surface 16 to the second surface 18, and a height F (FIG. 3) extending from the third surface 28 to the fourth surface 30. In such examples, one or more additional sensors may be disposed at, along, and/or proximate the third surface 28 or the fourth surface 30.

The patch 10 may be made from any substantially rigid medically approved material known in the art. Such materials may include, for example, plastics, rubber, polymers, synthetic materials, cloth, mesh, and/or combinations thereof. For example, the patch 10 may be made from materials similar to removable bandages or other like materials. These materials may allow for breathability during use and for easy disposal once use is complete. In addition, such patch materials may be substantially flexible, substantially light-weight, and/or relatively comfortable such that a patch 10 may be disposed on and/or removably attached to the forehead 12 of a subject 14 for extended periods of time. To assist with such removable connection, any known adhesive may be disposed on at least a portion of the first surface 16. Alternatively, one or more elastic straps, headbands, belts, ties, or the like may be connected to at least a portion of the patch 10 to assist in removably attaching the patch 10 to the forehead 12.

The patch 10 may have a known thermal resistance, and such thermal resistance may depend upon, for example, the thickness A of the patch 10 as well as the one or more materials utilized to form the patch 10. The thermal resistance of the plastics, rubber, polymers, or other materials used to form the patch 10 may be known in the art, and the sub-skull temperature and/or other core temperature determined in accordance with one or more of the example methods described herein may be calculated based upon the thermal resistance of at least a portion of the patch 10. For example, as shown in FIG. 3, the first sensor 24 may be separated from the second sensor 26 by material 46 having a known thermal resistance. In such embodiments, the material 46 may be the material used to form the patch 10. In other embodiments, however, the material 46 may comprise an additional piece of plastic, rubber, polymer, or other material, having a known thermal resistance, embedded within the patch 10. In any of the embodiments described herein, a core temperature of the subject 14 may be determined based at least partly on the temperatures measured by the first and second sensors 24, 26, and the thermal resistance of the material 46. In such embodiments, the core temperature of the subject 14 may also be determined based at least partly on the distance by which the first sensor 24 is spaced from the second sensor 26. In such examples, this distance may comprise a thickness G and/or other dimension of the material 46 spacing the first sensor 24 from the second sensor 26.

Moreover, example patches 10 of the present disclosure may be made from more than one material, and each portion of the patch 10 may have a unique thermal resistance depending upon the materials utilized to form the particular portion of the patch 10 and/or the relative thickness of the portion. For example, the material 46 separating the first and second sensors 24, 26 may be made from a first material, and the remainder of the patch 10 (or at least a second portion of the patch 10) may be made from a second material different than the first material. In such an example embodiment, the different portions of the patch 10 may have unique different thermal resistances. The different thermal resistances of each portion of the patch 10 may be taken into account when calculating, for example, the core temperature of the subject 14.

With continued reference to FIG. 3, in some examples the patch 10 may further include one or more wireless transmitters 32. Such transmitters 32 may comprise, for example, one or more transponders, transceivers, radio-frequency identification (RFID) coils, and/or other components configured to receive signals, power, and/or information from a remote source, such as a remote controller, a hand-held reader, or other such device. Such transmitters 32 may also comprise one or more devices configured to transmit signals, data, and/or other information to remote receivers. For example, a transmitter 32 of the patch 10 may be configured to wirelessly transmit information corresponding to one or more sensed temperatures to a remote computer, controller, reader, or other device utilized in the calculation of sub-skull temperatures and/or other core temperatures of the subject 14. An example remote device 58 is illustrated in FIG. 7. Such example transmitters 32 may facilitate communication with remote readers or other remote devices 58 using, for example, radio, infrared, wireless, WI-FI®, BLUETOOTH®, and/or other like technologies. Accordingly, such a transmitter 32 may enable noncontact monitoring of subjects 14 fitted with the patch 10, in relatively close proximity (e.g., within a hospital examination room and/or within a distance of several feet). Such a transmitter 32 may also enable monitoring of subjects 14 fitted with the patch 10 from one or more remote locations within, for example, a hospital or other healthcare facility. In addition, such a transmitter 32 may facilitate a wireless network connection with one or more routers, servers, or the like.

In such an example embodiment, the transmitter 32 may enable a healthcare professional to monitor one or more conditions of the subject 14 remotely via a data and/or internet connection or the like. Although not shown in FIGS. 2 and 3, it is understood that such a patch 10 may also include one or more USB ports, communication terminals, or other like components configured to facilitate connecting the patch 10 to one or more computers, controllers, monitors, servers, routers, or other like monitoring devices via one or more cables, wires, leads, or other like connection devices.

In example embodiments, the transmitter 32 may comprise a component of a control circuit within the patch 10. For example, the transmitter 32 may be electrically, operably, and/or otherwise connected to the controller 21 via one or more switches 34. Additionally, the transmitter 32 may be electrically, operably, and/or otherwise connected to the first and second sensors 24, 26 via the switch 34 and/or via the controller 21. Via such connections, the transmitter 32 may be configured to provide power to and/or otherwise activate the first sensor 24 and/or the second sensor 26 during operation of the patch 10.

For example, in embodiments in which the transmitter 32 comprises an RFID coil, the transmitter 32 may be energized by passing an RFID reader or other such device 58 in close proximity thereto. Upon being energized, the transmitter 32 may direct power to at least one of the first and second sensors 24, 26, via the controller 21, thereby activating the at least one of the first and second sensors 24, 26. In response to such activation, the at least one of the first and second sensors 24, 26 may sense, detect, and/or otherwise determine a respective temperature, and may direct one or more signals to the transmitter 32 indicative of such temperature. In an example embodiment, such signals may be directed to the transmitter 32 via the controller 21, and the transmitter 32 may direct such signals to the RFID reader or other device 58. Alternatively, such signals may be directed from the at least one of the first and second sensors 24, 26 to the controller 21. At least partly in response to receiving such signals, the controller 21 may determine, among other things, a core temperature of the subject 14 based at least partly on the temperatures determined by the at least one of the first and second sensors 24, 26. The controller 21 may then direct a signal indicative of the determined core temperature to the transmitter 32, and the transmitter 32 may provide a signal to the RFID reader or other device 58 indicative of the determined core temperature. In still further example embodiments, the circuit described above may include one or more modulators, filters, amplifiers, signal conditioners, and/or other circuit components (not shown). Such components may assist in, among other things, providing information from the first and second sensors 24, 26 to the controller 21 and/or to the transmitter 32.

As noted above, in example embodiments the patch 10 may include a conductor 36 associated with the first surface 16. In such embodiments, the first sensor 24 may be configured to determine a temperature and/or other characteristics of the conductor 36. As shown in FIG. 3, the conductor 36 may comprise a front surface 38 disposed substantially parallel to the second surface 18 of the patch 10. The conductor 36 may also include a top surface 40 disposed substantially perpendicular to the front surface 38, and a bottom surface 42 opposite the top surface 40. The conductor 36 may further include a back surface 44 opposite the front surface 38. In any of the example embodiments described herein, the conductor 36 may comprise a substantially planar sheet of conductive material such as copper, gold, and/or any other metal or alloy. In still further embodiments, the conductor may comprise a conductive liquid or gel disposed within and/or contained by the patch 10. In any of the examples described herein, the patch 10 may define one or more cavities, and the conductor 36 may be at least partially disposed in one or more such cavities.

In some examples, at least part of the conductor 36 may extend substantially coplanar with the first surface 16 of the patch 10. In such examples, at least part of the conductor 36, such as at least part of the front surface 38 may form at least part of the first surface 16 of the patch 10. As noted above, the patch 10 may also include one or more additional barriers or other components overlaying at least a portion of the conductor 36 so as to protect the conductor 36 from contamination caused by contact between the conductor 36 and the skin and/or other body surface of the subject 14. Alternatively, as shown in FIG. 3 at least part of the conductor 36, such as the front surface 38, may be spaced from the first surface 16 of the patch 10 by a distance B. For example, the conductor 36 may be embedded substantially within the patch 10, and a portion of the patch material may space the front surface 38 of the conductor 36 from the first surface 16 of the patch 10 by the distance B.

As shown in FIG. 3, the front surface 38 of an example conductor 36 may be spaced from the back surface 44 of the conductor 36 by a thickness C of the conductor extending from the front surface 38 to the back surface 44. In some examples, it may be desirable to minimize the thickness C of the conductor 36 in order to assist in maximizing heat transfer between the skin surface on which the patch 10 is disposed and the conductor 36. In some examples, the thickness C may be between approximately 0.001 mm and approximately 5 mm. Additionally, the top surface 40 of the conductor 36 may be spaced from the bottom surface 42 of the conductor 36 by a height D of the conductor 36 extending from the top surface 40 to the bottom surface 42.

Regardless of the particular configuration of the conductor 36, the conductor 36 may be positioned at any location relative to, for example, the first surface 16, third surface 28, and/or fourth surface 30 of the patch 10 to maximize the usefulness of the temperature determination made by, for example, the first sensor 24. For example, minimizing the distance B by which the front surface 38 of the conductor 36 is spaced from the first surface 16 of the patch 10 may improve the correlation between the temperature of the conductor 36 sensed by the first sensor 24 and the actual temperature of the skin surface on which the patch 10 is disposed. Improving this correlation may improve the accuracy of the sub-skull and/or other core temperature determinations made using the patch 10.

Additionally, in some example embodiments it may be desirable to maximize the height D of the conductor 36 in order to maximize the surface area of the conductor 36 available for interaction with the skin surface on which the patch 10 is disposed. By maximizing the surface area, for example, inaccuracies in skin temperature measurement caused by skin irregularities, air pockets formed between the skin surface and the first surface 16 of the patch 10, and/or other environmental factors associated with skin temperature measurement can be mitigated. In such examples, the first sensor 24 may comprise one or more temperature sensing elements configured to determine multiple respective temperatures of the conductor 36. The thermal conductivity of layer 36 improves the conduction of heat from the skin surface to the first temperature sensor 24 and provides a small thermal mass that creates a low-pass filter on small perturbations, for example, if the sensor position changes slightly. In some embodiments, such sensing elements may be configured to determine the respective temperatures of the front surface 38 of the conductor 36. In such examples, the controller 21, the sensor 24, and/or other components of the various systems described herein may determine the temperature of the conductor 36 by averaging and/or otherwise processing each of the temperatures determined by the multiple sensing elements of the first sensor 24. Such processing may assist in mitigating the inaccuracies in skin temperature measurement described above.

Further, since portions of the patch 10, such as the third surface 28 and/or the fourth surface 30 can be susceptible to variations in temperature caused by ambient conditions, it may also be desirable to space at least a portion of the conductor 36 from such portions of the patch 10. Such spacing may be achieved by, for example, modifying the height D of the conductor 36 and/or by modifying the height F of the patch 10. As shown in FIG. 3, the top surface 40 of the conductor 36 may be spaced from the third surface 28 by a first distance $E_1$, and the bottom surface 42 of the conductor 36 may be spaced from the fourth surface 30 of the patch 10 by a second distance $E_2$ substantially equal to the first distance $E_1$. Spacing, for example, the top and bottom surfaces 40, 42 of the conductor 36 from the third and fourth surfaces 28, 30 of the patch 10 in this way may assist in minimizing inaccuracies in skin temperature measurement caused by at least one of the third and fourth surfaces 28, 30 having a temperature that is greater than or less than the actual temperature of the skin surface on which the patch 10 is disposed.

Collectively, the first and second distances $E_1$, $E_2$ may be referred to as a "pullback" of the patch 10, and in general, such a pullback may be defined by the distance by which one or more surfaces or edges of the conductor 36 is spaced from one or more corresponding adjacent surfaces or edges of the patch 10. It is understood that by increasing the pullback of the patch 10, inaccuracies in skin temperature measurement caused by, for example, the relative coolness of the third and fourth surfaces 28, 30 of the patch 10 may be minimized. However, increasing the first and second distances $E_1$, $E_2$ may also decrease the overall height D of the conductor 36, and may result in an overall decrease in the surface area of the front surface 38. Accordingly, in some examples, increasing the pullback of the patch 10 may result in a patch 10 that is more susceptible to inaccuracies in skin temperature measurement caused by skin irregularities, air pockets formed between the skin surface and the first surface 16 of the patch 10, and/or other environmental factors associated with skin temperature measurement.

As noted above, the second sensor 26 may be configured to determine at least one additional temperature associated with the patch 10. In some examples, such an additional temperature may comprise a temperature of at least a portion of the patch 10 spaced from the first surface 16. In example embodiments, such an additional temperature may comprise a temperature of and/or otherwise associated with the second surface 18. Additionally, in some example embodiments such an additional temperature may comprise an ambient temperature associated with the environment in which the patch 10 is used. In embodiments in which the additional temperature determined by the second sensor 26 comprises an ambient temperature and/or a temperature of and/or otherwise associated with the second surface 18, the second sensor 26 may be disposed proximate, adjacent to, at, and/or on the second surface 18 of the patch 10 in order to minimize and/or eliminate inaccuracies in such temperature measurements caused by, for example, the temperature of the patch 10 itself. On the other hand, in embodiments in which the additional temperature determined by the second sensor 26 comprises a temperature of at least a portion of the patch 10 spaced from the first surface 16, the second sensor 26 may be spaced from the second surface 18 by a distance H. Spacing the second sensor 26 from the second surface 18 in this way may assist in minimizing and/or eliminating inaccuracies in temperature measurements caused by, for example, ambient temperatures and/or the temperature of the second surface 18. The system may infer the cause of a temperature change to be internal (the patient) or external (ambient) by the causal relationship between detected changes on the first sensor 24 and second sensor 26. As an example, a fever spike would first sensor 24 to increase in temperature and then as the heat flux flows through the system, second sensor 26 would increase slightly. In contrast, if the patient is below an air vent and hot air begins to flow, then the second sensor 26 would heat without the first sensor 24 first detecting a temperature increase. The system may adjust the formulae and/or weightings used to calculate temperature based on the magnitude and causal relationship between temperature readings. The system may also time average readings or otherwise filter the raw sensor data to improve the temperature reading accuracy.

FIG. 4 illustrates the first surface 16 of an example patch 10 in which at least a portion (e.g., the front surface 38) of the conductor 36 extends substantially coplanar with and/or forms at least a portion of the first surface 16 of the patch 10. As shown in FIG. 4, in some examples the conductor 36 may include a first side surface 47 extending substantially perpendicular to the top surface 40 and/or the bottom surface 42. Additionally, the conductor 36 may include a second side surface 49 opposite the first side surface 47. In such examples, the second side surface 49 may also extend substantially perpendicular to the top surface 40 and/or the bottom surface 42, and may be substantially parallel to the first side surface 47. In such examples, the conductor 36 may have a width I extending from the first side surface 47 to the second side surface 49. Patch 10 need not be a quadrilateral and need not be a regular polygon. It may have planar cross-sections, including but not limited to: an ellipse, rectangle, superellipse, pentagon, hexagon, parallelogram, trapezoid, and the like.

Additionally, as shown in FIG. 4 the patch 10 may further include a fifth surface 48 substantially perpendicular to at least one of the first and third surfaces 16, 28 of the patch 10. The patch 10 may also include a sixth surface 50 opposite the fifth surface 48. In such examples, the sixth surface 50 may also be substantially perpendicular to at least one of the first and third surfaces 16, 28 of the patch 10, and may be substantially parallel to the fifth surface 48. Thus, the patch 10 may have a width K extending from the fifth surface 48 to the sixth surface 50. In such examples, the first side surface 47 of the conductor 36 may be spaced from the fifth surface 48 of the patch 10 by a third distance ii, and the second side surface 49 of the conductor 36 may be spaced from the sixth surface 50 of the patch 10 by a fourth distance $J_2$. In some examples, the third and fourth distances $J_1$, $J_2$ may be substantially equal to one another. Alternatively, in further example embodiments, the fourth distance $J_2$ may be different from the third distance $J_1$. Additionally, in example embodiments at least one of the first distance $E_1$ or the second distance $E_2$ may be substantially equal to at least one of the third distance ii or the fourth distance $J_2$. In any of the example embodiments described herein, at least one of the first, second, third, or fourth distance $E_1$, $E_2$, $J_1$, $J_2$ may be between approximately 0 mm and approximately 8 mm.

As described above with respect to the first and second distances $E_1$, $E_2$, collectively, the third and fourth distances $J_1$, $J_2$ may be referred to as a "pullback" of the patch 10, and in general, such a pullback may be defined by the distance by which one or more surfaces or edges of the conductor 36 is spaced from one or more corresponding adjacent surfaces or edges of the patch 10. It is understood that by increasing the pullback of the patch 10 associated with the third and fourth distances $J_1$, $J_2$, inaccuracies in skin temperature measurement caused by, for example, the relative coolness of the fifth and sixth surfaces 48, 50 of the patch 10 may be minimized. However, increasing the third and fourth distances $J_1$, $J_2$ may also decrease the overall width I of the conductor 36, and may result in an overall decrease in the surface area of the front surface 38. Accordingly, in some examples, increasing the pullback of the patch 10 associated with the third and fourth distances $J_1$, $J_2$ may result in a patch 10 that is more susceptible to inaccuracies in skin temperature measurement caused by skin irregularities, air pockets formed between the skin surface and the first surface 16 of the patch 10, and/or other environmental factors associated with skin temperature measurement.

As noted above, the position of the conductor 36 relative to various surfaces and/or portions of the patch 10 may have an effect on the temperature determinations made by one or more of the sensors 24, 26 described herein. As will be described below, the thickness A of the insulator may have an effect on such temperature determinations. The thickness C, height D, width I, size, material, and/or other configurations of the conductor 36 may also have an effect on such temperature determinations. FIGS. 5 and 6 provide temperature plots illustrating such effects.

For example, FIG. 5 is a temperature plot illustrating a series of sample surface temperatures $T_s$ measured with example patches 10 including one or both of the first and second sensors 24, 26. For testing purposes, the temperature of the sample surface being measured was held constant at approximately 96° Fahrenheit. The example patches 10 utilized to measure the temperatures $T_s$ illustrated in FIG. 5 each included an insulator with a thickness A of 5 mm and a conductor 36 with thickness 0.4 mm. Additionally, the example patches 10 included pullbacks (associated with the first and second distances $E_1$, $E_2$,) of 0, 2, 4, 5, 7, and 8 mm, respectively. As can be seen in the temperature plot of FIG. 5, for patches 10 having conductors 36 with respective thicknesses C of 5 mm, a pullback associated with the first and second distances $E_1$, $E_2$, of 5 mm resulted in a measured temperature $T_s$ that most closely corresponded to the actual temperature of the sample surface being measured.

FIG. 6 is another temperature plot illustrating a series of sample surface temperatures $T_s$ measured with example patches 10 including one or both of the first and second sensors 24, 26. For testing purposes, the temperature of the sample surface being measured was held constant at approximately 96° Fahrenheit. The example patches 10 utilized to measure the temperatures $T_s$ illustrated in FIG. 6 each included an insulator with a thickness A of 3 mm and a conductor 36 with thickness 0.4 mm. Additionally, similar to the patches described above with respect to FIG. 5, the example patches 10 associated with the temperature plot of FIG. 6 included pullbacks (associated with the first and second distances $E_1$, $E_2$,) of 0, 2, 4, 5, 7, and 8 mm, respectively. As can be seen in the temperature plot of FIG. 6, for patches 10 having insulators with respective thicknesses A of 3 mm, a pullback associated with the first and second distances $E_1$, $E_2$, of 5 mm resulted in a measured temperature $T_s$ that most closely corresponded to the actual temperature of the sample surface being measured. Physical factors of the amount of pull-back as well as the percentage of the surface covered by the conductor 36 (e.g., 100%*(D*I/K*F) affect the fringing fields. In some embodiments, example pullbacks described herein may decrease thermal coupling of the conductor to the ambient. In such examples, the conductor 36 may be substantially centered on the patch 10 for patches 10 of size about 25 mm×25 mm. For relatively large patches 10, the conductor 36 could be offset from the center of the patch 10 and still not be near the edge. In example embodiments in which the patch 10 is relatively small, the conductor 36 may also be relatively small and/or the pullback may be relatively small. In the limit of no pullback ($E_1=E_2=J_1=J_2=0$) and in the limit of a D and I approaching 0 (approaching no conductor), there is decreased benefit of adding the conductor 36. As a result, in some examples, relatively small patches 10 may benefit less from the presence of the conductor 36. In the limit of a relatively large insulator, there may be little additional gain from making the conductor 36 large, so the pullback will tend to increase as the size of the patch 10 increases. A conductor 36 that is thicker in the middle than the edges provides a method to have thermal mass and larger area while minimizing the edged effects because the thermal resistance of the edges is reduced due to the thinness of the conductor 36 in that region. The more perfect the adhesion between patch 10 and the subject, the less the fringing effect as the conductor 36 is better shielded from ambient conditions with better adhesion. Additionally, with this configuration, the thicker insulator (the insulator associated with the temperature plot of FIG. 5 having a thickness A of 5 mm) generally resulted in more accurate temperature measurements (e.g., measured temperatures $T_s$ close to the actual temperature of the sample surface). With a thicker insulator there is less heat transfer from the subject to the exterior environment (this environment includes the patch 10), so the system tends to be closer to the subject temperature. The thinner insulator tends to have a longer thermal time constant. The system may be designed using different thicknesses and sizes of insulators and with different thicknesses and sizes of conductive material to optimize response time vs accuracy.

FIG. 7 illustrates an example system of the present disclosure. As shown in FIG. 7, such an example system may include at least one patch 10. An example system may also include a device 58, such as an RFID reader, a handheld control device, and/or other noncontact sensing device. Such a device 58 is illustrated in FIG. 7 as being a handheld device, carried by a hand 60 of a user. Such devices 58 may be configured to provide power to at least one of the first and second sensors 24, 26 by disposing the device 58 at a distance less than or equal to a minimum distance L from the transmitter 32. Additionally, the transmitter 32 may be configured to provide information indicative of respective temperatures determined by the first and second sensors 24, 26, and/or one or more sub-skull or other core temperature values determined by the controller 21, to the device 58 when the device 58 is disposed at a distance less than or equal to the distance L from the transmitter 32. In some examples, the distance L may be, for example, the sensitivity range of the device 58 and/or the transmission range of the transmitter 32.

As shown in FIG. 7, in some examples the patch 10 may be removably disposed on the forehead 12 of a subject 14, and may be removably attached to an outer surface 56 and/or other measurement site on the layer of skin 54 covering the frontal skull bone 52. In such examples, the conductor 36 may be in contact with the outer surface 56 of the layer of skin 54, thereby improving the transmission of heat from the surface 56 to the conductor 36. Such intimate contact between the conductor 36 and the surface 56 may also increase the relative temperature of the first sensor 24 configured to determine the temperature of the conductor 36.

Additionally, such improved transmission of heat and/or increases in the relative temperature of the first sensor 24 may reduce and/or minimize the dependence upon a correction factor when calculating a sub-skull temperature and/or other core temperature of the subject 14. Reducing such dependence upon a correction factor for sub-skull and/or core temperature value determinations may be beneficial in order to avoid errors in the correction factor caused by, among other things, environmental factors such as variations in ambient temperature. Additionally, correction factors such as the ratio between a thermal resistance $R_s$ of the layer of skin 54 and a thermal resistance $R_I$ of the material 46 separating the first sensor 24 from the second sensor 26 may have a certain level of inherent error notwithstanding other errors that may be the result of environmental influences. Thus, reducing the dependence upon such correction factors may improve the accuracy of the sub-skull temperature and/or other temperature determinations made using the systems described herein.

FIGS. 8 and 9 include flowcharts illustrating various example methods of the present disclosure. For example, FIG. 8 includes a flowchart 100 illustrating an example method of manufacturing a system of the present disclosure. As noted above with respect to FIG. 7, such a system may include a patch 10, at least one sensor, a conductor 36, and/or any other components described herein with respect to FIGS. 1-7. Additionally, such a system may include one or more noncontact sensing devices 58 configured to communicate with and/or otherwise interact with the patch 10 and/or components thereof. As shown in FIG. 8, at step 102 such an example method of manufacturing may include providing a patch 10 defining a first surface 16 and a second surface 18 opposite the first surface 16. As noted above, in some example embodiments the first surface 16 may be removably attachable to a surface 56 of a layer of skin 54 of a subject 14, and/or to any other measurement site. Such an example method may also include, at step 104, and connecting a conductor 36 to the patch 10 at a location spaced from the second surface 18. For example, the conductor 36 may be disposed proximate the first surface 16 so as to maximize the transmission of heat (e.g., a heat flow rate) from the surface 56 to the conductor 36 when the patch 10 is attached to the surface 56. In some examples, step 104 may include positioning the conductor 36 such that the front surface 38 of the conductor 36 extends substantially coplanar with the first surface 16 of the patch 10. In such embodiments, the conductor 36 may form at least a portion of the first surface 16 of the patch 10. In additional examples, step 104 may also include positioning the conductor 36 such that the top surface 40 of the conductor 36 is spaced from the third surface 28 of the patch 10 by a first distance $E_1$. Step 104 may further include positioning the conductor 36 such that the bottom surface 42 of the conductor 36 is spaced from the fourth surface 30 of the patch 10 by a second distance $E_1$ substantially equal to the first distance $E_1$. By spacing the top and bottom surfaces 40, 42 of the conductor 36 from the third and fourth surfaces 28, 30, respectively, errors in temperature measurement caused by environmental influences such as, for example, ambient temperature may be minimized and/or substantially eliminated. For example, in circumstances in which the temperature of one or more sides, surfaces, edges, and/or other portions of the patch 10 is increased or decreased due to ambient temperature conditions, the effect of such increases or decreases in temperature can be minimized by spacing surfaces and/or other portions of the conductor 36 from such portions of the patch 10.

Example methods of the present disclosure may also include, at step 106, operably connecting the first sensor 24 to the patch 10. In particular, the first sensor 24 may be configured to determine a temperature of the conductor 36, and in such examples, the first sensor 24 may be electrically, mechanically, and/or otherwise operably connected to the conductor 36 in order to facilitate such temperature determinations. For example, the first sensor 24 may be operably connected to the conductor 36 so as to determine the temperature of at least a portion of at least one of the front surface 38 or the back surface 44. In example embodiments in which the first sensor 24 includes one or more sensing elements, each of the sensing elements may be operably connected to the conductor 36 at step 106.

The method may also include, at step 108, operably connecting the second sensor 26 to the patch 10. For example, at step 108, the second sensor 26 may be spaced from the first sensor 24 by material 46 having a known thermal resistance. In some examples, the material 46 may comprise at least a portion of the patch 10. Additionally, in such examples the second sensor 26 may be configured to determine at least one additional temperature associated with the patch 10. For example, whereas the first sensor 24 may be positioned and/or otherwise configured to determine one or more temperatures associated with the conductor 36, the second sensor 26 may be positioned and/or otherwise configured to determine a temperature of at least a portion of the patch 10 spaced from the conductor 36. In such examples, such a portion of the patch 10 may include the second surface 18 and/or or more portions of the patch 10 proximate the second surface 18.

In example embodiments, a method of manufacturing may also include, at step 110, electrically, mechanically, operably, and/or otherwise connecting the wireless transmitter 32 to the patch 10. In particular, step 110 may include, among other things, operably connecting the wireless transmitter 32 to at least one of the first and second sensors 24, 26. In such examples, the wireless transmitter 32 may be configured to wirelessly provide a first temperature, such as a temperature of at least a portion of the conductor 36, determined by the first sensor 24 to one or more noncontact sensing devices 58 such as via Bluetooth, radio transmission, Wi-Fi, and/or other communication means. For example, in some embodiments the wireless transmitter 32 may comprise one or more RFID coils configured to wirelessly provide information to an RFID reader or other noncontact sensing device 58 via radio transmission. Wireless transmitter 32 may also be configured to wirelessly provide an additional temperature determined by the second sensor 26 to the device 58. In such examples, one or more processors, controllers, and/or other components of the device 58 may be configured to determine one or more sub-skull temperatures or other such core temperatures of the subject 14 based at least partly on at least one of the temperature of the conductor 36 determined by the first sensor 24 or the additional temperature determined by the second sensor 26.

In still further examples, the wireless transmitter 32 may be configured to wirelessly provide one or more sub-skull temperatures or other such core temperatures of the subject 14 to the noncontact sensing device 58. In such examples, such temperatures may be determined by one or more controllers 21 associated with the patch 10 based at least partly on at least one of the temperature of the conductor 36 determined by the first sensor 24 or the additional temperature determined by the second sensor 26.

Accordingly, some example methods of manufacturing may also include connecting, at step 112, a controller 21 to the patch 10. For example, step 110 may include mounting the controller 21 within the patch 10 and operably connecting at least one of the first sensor 24 or the second sensor 26 to the controller 21. In such examples, the at least one of the first sensor 24 or the second sensor 26 may be configured to transmit determined temperatures and/or other information to the controller 21, and the controller 21 may be configured to calculate a sub-skull temperature and/or other core temperature of the subject 14 based on such temperatures. Additionally, as will be described in further detail below, the controller 21 may be configured to calculate a sub-skull temperature and/or other core temperature of the subject 14 based at least partly on such temperatures and based on the thermal resistance of the material 46 spacing the first sensor 24 from the second sensor 26. In still further examples, such core temperature determinations may also be made based on one or more additional inputs, such as a measured ambient temperature, an average temperature based on a plurality of patch temperature and/or skin surface 56 temperature measurements, a blood oxygen concentration measurement, rate of change of temperature of the first sensor 24 compared to the second sensor 26, causal relationship between temperature changes detected by the first sensor 24 and the second sensor 26, air velocity detectors that determine if heating and/or air conditioning breezes are present, and/or other measurements that improve the precision of the measurement.

FIG. 9 includes a flowchart 200 illustrating another example method of the present disclosure. In particular, the flow chart illustrates an example method of determining a sub-skull and/or other core temperature of the subject 14. As illustrated by FIG. 9, in an example embodiment a sub-skull and/or other core temperature may be determined by sensing one or more temperatures associated with the forehead skin 54 and/or of the patch 10 while the patch 10 is at least temporarily contacting and/or removably attached to the forehead 12. For example, in order to calculate a sub-skull temperature, a temperature of the first surface 16 and/or of the conductor 36 contacting the forehead 12 may be sensed, along with a temperature of another portion of the patch 10 spaced from the forehead 12. In additional example embodiments, such temperature measurements may be taken at two different predetermined levels, depths, or locations within the patch 10, and along a heat transfer flow path within the patch 10 (e.g. between the surface 56 and one or both of the sensors 24, 26). In such embodiments, the sensors 24, 26 may be positioned at such predetermined locations within the patch 10 for temperature measurement. According to basic heat transfer theory, the quantitative value of heat flow (q) is generally equal to the amount of heat energy passing through a given system over time. Such heat flow is governed by the resistance of the system as well as the temperature drop across the system. In the case of a subject 14, the sub-skull temperature and/or other core temperature of the subject 14 can be solved for utilizing these heat flow relationships.

With reference to the flowchart 200 illustrated in FIG. 9, an example method of the present disclosure may include removably attaching the patch 10 to a skin surface 56 of the subject 14 at step 202. For example, the first surface 16 of the patch 10 may be at least temporarily adhered to the surface 56 of the forehead 12 and/or to any other measurement site of the subject 14, such as an alternate skin surface. At step 204, the wireless transmitter 32 of the patch 10 may wirelessly receive one or more activation signals from a remote device. For example, the wireless transmitter 32 may receive one or more control signals from one or more noncontact sensing devices 58, such as via Bluetooth®, radio transmission, Wi-Fi®, and/or other communication means. As noted above, in some embodiments the wireless transmitter 32 may comprise one or more RFID coils. In such embodiments, at step 202 the wireless transmitter 32 may receive power from an RFID reader or other noncontact sensing device 58 when the device 58 is disposed at a distance less than or equal to the distance L described above with respect to FIG. 7. Power and/or other activation signals received by the wireless transmitter 32 at step 204 may energize and/or otherwise activate components of the patch 10 operably connected to the wireless transmitter 32 including, for example, the controller 21, the first sensor 24, and/or the second sensor 26.

For example, at step 206 the controller 21 may control and/or otherwise cause the first sensor 24 to determine a first temperature associated with the conductor 36. In particular, the activation signal received by the wireless transmitter 32 at step 204 may cause the controller 21 to perform one or more functions, operations, and/or methods. Such methods may include, for example, directing one or more components of the patch 10 to perform one or more temperature determinations. For example, at step 206 the first sensor 24 may sense and/or otherwise determine a temperature of the conductor 36 in response to one or more control signals received from the controller 21. Such temperatures may include, for example, one or more temperatures of the front surface 38 of the conductor 36 disposed proximate and/or in contact with the skin surface 56 of the subject 14. Additionally, at step 206 the first sensor 24 may provide one or more signals including information indicative of such temperatures to the controller 21 and/or to the wireless transmitter 32.

At step 208, the controller 21 may control and/or otherwise cause the second sensor 26 to determine an additional temperature associated with at least a portion of the patch 10 spaced from the conductor 36 and/or from the first surface 16 of the patch 10. In particular, the activation signal received by the wireless transmitter 32 at step 204 may cause the controller 21 to direct the second sensor 26 to sense and/or otherwise determine such an additional temperature. The additional temperature determined by the second sensor 26 in response to one or more control signals received from the controller 21 may include, for example, one or more temperatures of a portion of the patch 10 proximate and/or including the second surface 18. Such additional temperatures may be approximately equal to an ambient temperature in some situations. Additionally, at step 208 the second sensor 26 may provide one or more signals including information indicative of such additional temperatures to the controller 21 and/or to the wireless transmitter 32.

In some examples, such methods may also include calculating and/or otherwise determining, at step 210, a sub-skull temperature and/or other core temperature of the subject 14 based at least partly on the respective temperatures determined by the first and second sensors 24, 26. Such methods may also include providing, at step 212, information determined by at least one of the first sensor 24, the second sensor 26, or the controller 21 to the noncontact sensing device 58. Such information may include, for example, the respective temperatures determined by the first and second sensors 24, 26 and/or the thermal resistance of the material 46 separating the first sensor 24 from the second sensor 26. In such examples, a controller, processor, and/or other component of the device 58 may determine a sub-skull temperature and/or other core temperature of the subject 14 based at least partly on the information provided at step 212.

In further embodiments, the information provided at step 212 may also include, for example, a sub-skull temperature and/or other core temperature of the subject 14 determined by the controller 21 at step 210. In such examples, the controller 21 of the patch 10 may receive signals from the first and second sensors 24, 26 indicative of respective temperatures determined by the sensors 24, 26. The controller 21 may determine, at step 210, a sub-skull temperature and/or other core temperature of the subject 14 based at least partly on the information received from the first and second sensors 24, 26 and/or the thermal resistance of the material 46 separating the first sensor 24 from the second sensor 26. At step 212, the controller 21 may wirelessly provide the sub-skull temperature and/or other core temperature of the subject 14 to the device 58 via the wireless transmitter 32.

In each of the example embodiments described herein, the controller 21 of the patch 10 and/or one or more processors, controllers, or other components of the device 58 may calculate the amount of heat flowing out of the forehead 12, and thus the sub-skull temperature $T_{sub\text{-}skull}$ and/or other core temperature of the subject 14, according to the following equation:

$$T_{sub\text{-}skull} = T_1 + R(T_1 - T_2).$$

In the above equation, "$T_1$" may be the first temperature determined by the first sensor 24 at step 206, and "$T_2$" may be the additional temperature determined by the second sensor 26 at step 208. Additionally, in the above equation "R" may be a constant that is estimated and/or empirically determined based upon the physical characteristics of the subject 14 and/or the patch 10. In particular, the constant R may be a thermal resistance associated with the skull bone 52 and/or skin 54 of the forehead 12. In an example embodiment, the constant R may represent the thermal resistance of the forehead 12 consisting of both the skull bone 52 and skin 54. The value of the constant R utilized in the sub-skull temperature and/or other core temperature calculation may vary within a relatively limited range based on one or more physical characteristics of the subject 14. For example, a range of constants R may be estimated and/or empirically determined based upon at least one of the age, weight, gender, and/or other characteristics of the subject 14, and the values of such constants R may have a variation on the order of approximately 20%. In determining the sub-skull and/or other core temperature of a particular subject 14, a constant R may be chosen based upon whether the subject 14 is a small child, an average-sized adult, a large adult, and/or an elderly adult. In addition, the chosen constant R may vary for males as opposed to females, in any of the above age ranges or categories.

The value of each constant R may also be based upon the thermal resistance of the patch 10, or at least a portion thereof. The thermal resistance of portions of the patch 10 may be dependent upon the physical construction and/or thermal characteristics of the patch 10 such as, for example, the materials used to form the patch 10 and/or the one or more thicknesses thereof. In an example embodiment, the constant R may comprise a correction factor that is calculated by dividing the thermal resistance of the forehead 12 by the thermal resistance of at least a portion of the patch 10. For example, the constant R may be equal to the thermal resistance $R_s$ of the layer of skin 54 divided by the thermal resistance $R_l$ of the material 46 separating the first sensor 24 from the second sensor 26. In still further embodiments, the constant R may be equal to a thermal resistance of the forehead 12 (e.g., a combined thermal resistance of the skull bone 52 and the layer of skin 54) divided by the thermal resistance $R_l$ of the material 46. In still further embodiments, the constant R may be equal to the thermal resistance of the system between the heat source (e.g., the brain) and the insulator, including the thermal resistance of the skull, skin, thermal contact resistance between the skin and the patch 10 divided by the thermal resistance $R_l$, of the material 46. In example embodiments, the constant R may be determined through experimentation and/or through one or more clinical trials utilizing different constructions and/or embodiments of the patch 10 to measure and/or calculate sub-skull temperatures and/or other core temperatures of subjects 14 having a variety of different ages, weights, genders, and/or other physical characteristics. A healthcare professional may determine which constant R to use for a given subject 14 and patch 10 using one or more look-up tables or other resources.

In additional example embodiments, the sub-skull temperature and/or other core temperature of the subject 14 may be determined based on one or more physical characteristics, conditions, and/or other metrics associated with the subject 14 and indicative of blood flow. For example, in calculating such a sub-skull temperature, a healthcare professional may measure, determine, and/or otherwise sense a metric indicative of blood flow at the forehead skin 54 of the subject 14. Significant blood flow proximate the first surface 16 of the patch 10 may cause error in temperature and/or other measurements obtained with the patch 10. For these reasons, it may be desirable and/or advantageous to avoid positioning the patch 10 proximate the temporal artery, or other veins or arteries of the subject 14. The forehead 12 of the subject 14 may be particularly well suited for calculating sub-skull temperature and/or other core temperatures according to the example methods described herein because the forehead 12 is generally free from such blood flow passageways. Accordingly, sensing a metric indicative of blood flow at the forehead skin 54 may assist in minimizing and/or substantially illuminating error in the temperature calculation.

Example systems of the present disclosure may provide advantages over existing temperature measurement devices and/or systems. For example, positioning the conductor 36 proximate, adjacent to, and/or substantially coplanar with the first surface 16 of the patch 10 may maximize the heat transfer between the skin surface 54 and the various components of the patch 10. Increasing the surface area of at least the front surface 38 of the conductor 36 in communication with the skin surface 54 may further improve the heat transfer characteristics of the patch 10. Additionally, spacing the top and bottom surfaces 40, 42 of the conductor 36 from the third and fourth surfaces 28, 30 of the patch 10, respectively, may minimize and/or substantially eliminate temperature measurement errors caused by ambient and/or other environmental conditions. As described herein, the thickness C, height D, width I, and/or other characteristics of the conductor 36 may be tuned in accordance with the considerations and techniques discussed above in order to maximize the accuracy of temperature measurements made using the patch 10. The effects of each of these characteristics may contribute to the overall accuracy of such measurements. Moreover, the wireless transmitter 32, controller 21, and/or other components of the patch 10 may receive power from and may wirelessly communicate with the noncontact sensing device 58. Such wireless power transfer and communication may facilitate substantially nonintrusive monitoring of the subject 14, and as a result, may improve patient comfort in healthcare settings, provide early detection of febrile spikes thereby alerting clinicians of a need to attend to the patient, decrease the time it takes to measure routine vital signs, and decrease the time in the hospital. At home, use of the various systems described herein allows parents peace of mind as the system automatically measures and reports temperatures, alerting the parents when a sick child's temperature reaches a critical level.

The invention has been described in detail with particular reference to a presently preferred embodiment, but it will be understood that variations and modifications can be effected within the spirit and scope of the invention. The presently disclosed embodiments are, therefore, considered in all respects to be illustrative and not restrictive. The scope of the invention is indicated by the appended claims, and all changes that come within the meaning and range of equivalents thereof are intended to be embraced therein.

What is claimed is:

1. A system, comprising:
a patch defining a first surface and a second surface opposite the first surface, wherein the first surface is removably attachable to skin of a subject, the patch comprising:
a conductor associated with the first surface,
a first sensor configured to determine a temperature of the conductor,
a second sensor configured to determine an additional temperature, wherein the first sensor is separated from the second sensor by a material having a first thermal resistance,
an RFID antenna operably connected to the first sensor and the second sensor, wherein the RFID antenna is configured to provide at least one of the temperature of the conductor, the additional temperature, or a core temperature of the subject to an RFID reader; and
a controller operably connected to the first sensor, the second sensor, and the RFID antenna, the controller being configured to:
activate using power received via the RFID antenna,
cause power provided via the RFID antenna to be directed to the first sensor and the second sensor, and
determine, using the power received via the RFID antenna, the core temperature of the subject based on the temperature of the conductor, the additional temperature, and the first thermal resistance of the material.

2. The system of claim 1, wherein the patch comprises an additional material having a second thermal resistance, and the second thermal resistance is different from the first thermal resistance.

3. The system of claim 1, the patch further comprising a third surface substantially perpendicular to the first surface, and a fourth surface opposite the third surface, the patch having a thickness extending from the first surface to the second surface, and a height extending from the third surface to the fourth surface, wherein:
the conductor extends substantially parallel to the second surface, and
substantially perpendicular to at least one of the third surface or the fourth surface.

4. The system of claim 3, wherein the conductor includes a top surface spaced from the third surface by a first distance, and a bottom surface opposite the top surface and spaced from the fourth surface by a second distance substantially equal to the first distance.

5. The system of claim 4, the patch further comprising a fifth surface substantially perpendicular to the first and third surfaces, and a sixth surface opposite the fifth surface, the patch having a width extending from the fifth surface to the sixth surface, wherein the conductor includes a first side surface spaced from the fifth surface by a third distance, and a second side surface opposite the first side surface and spaced from the sixth surface by a fourth distance substantially equal to the third distance.

6. The system of claim 5, wherein at least one of the first distance or the third distance is between approximately 0 mm and approximately 8 mm.

7. The system of claim 5, wherein the first distance is substantially equal to the third distance.

8. The system of claim 1, wherein the conductor includes a front surface spaced from the first surface by at least a portion of the patch.

9. The system of claim 1, wherein the conductor includes a front surface extending substantially coplanar with the first surface.

10. The system of claim 1, wherein the first sensor comprises a plurality of sensing elements configured to determine respective temperatures of a front surface of the conductor,
the front surface being disposed adjacent to the first surface of the patch, and
the controller being configured to determine the temperature of the conductor based on the respective temperatures.

11. The system of claim 10, wherein the temperature of the conductor comprises an average of the respective temperatures.

12. The system of claim 1, wherein the material is separate from and embedded within the patch, the material separating the first sensor from the second sensor.

13. The system of claim 12, wherein:
the first thermal resistance is different from a second thermal resistance of the patch, and
the first sensor is disposed between the material and the conductor.

14. A system, comprising:
a patch defining a first surface and a second surface opposite the first surface, wherein the first surface is removably attachable to skin of a subject, the patch comprising:
a conductor associated with the first surface,
a first thermistor configured to determine a temperature of the conductor,
a second thermistor configured to determine an additional temperature, wherein the first thermistor is separated from the second thermistor by a material having a first thermal resistance,
a transmitter operably connected to the first thermistor and the second thermistor, wherein the transmitter is configured to wirelessly provide at least one of the temperature of the conductor, the additional temperature, or a core temperature of the subject to a device separate from the patch; and
a controller operably connected to the first thermistor, the second thermistor, and the transmitter, the controller being configured to:
activate using power received wirelessly via the transmitter,
cause power provided via the transmitter to be directed to the first thermistor and the second thermistor, and
determine, using the power received wirelessly via the transmitter, the core temperature of the subject based on the temperature of the conductor, the additional temperature, and the first thermal resistance of the material.

15. The system of claim 14, wherein the transmitter is configured to provide power to at least one of the first thermistor and the second thermistor.

16. The system of claim 14, wherein the conductor comprises one of a metallic sheet or an electrically conductive gel.

17. The device of claim 14, wherein the conductor includes a front surface extending substantially parallel to the second surface, a back surface opposite the front surface, and a thickness extending from the front surface to the back surface, wherein the thickness is between approximately 0.001 mm and approximately 5 mm.

18. The system of claim 17, wherein the front surface extends substantially coplanar with the first surface.

19. The system of claim 14, the patch further comprising:
a third surface substantially perpendicular to the first surface,
a fourth surface opposite the third surface,
a fifth surface substantially perpendicular to the first and third surfaces, and
a sixth surface opposite the fifth surface, wherein the conductor includes:
a top surface spaced from the third surface by a first distance,
a bottom surface opposite the top surface and spaced from the fourth surface by a second distance substantially equal to the first distance,
a first side surface spaced from the fifth surface by a third distance, and
a second side surface opposite the first side surface and spaced from the sixth surface by a fourth distance substantially equal to the third distance.

* * * * *